United States Patent [19]

Suzuki et al.

[11] Patent Number: 4,629,450
[45] Date of Patent: Dec. 16, 1986

[54] CATHETER INTRODUCING INSTRUMENT

[75] Inventors: Tatsuo Suzuki, Yokohama; Atsushi Matsumoto, Fuji, both of Japan

[73] Assignee: Terumo Corporation, Tokyo, Japan

[21] Appl. No.: 731,082

[22] Filed: May 6, 1985

[30] Foreign Application Priority Data

May 9, 1984 [JP] Japan .................... 59-90890

[51] Int. Cl.$^4$ .................................. A61M 5/00
[52] U.S. Cl. ............................ 604/164; 128/343; 604/104; 604/167
[58] Field of Search .................... 604/51-53, 604/158-169, 104; 128/343

[56] References Cited

U.S. PATENT DOCUMENTS

| Re. 31,855 | 3/1985 | Osborne | 604/164 X |
|---|---|---|---|
| 4,014,333 | 3/1977 | McIntyre | 604/167 X |
| 4,052,989 | 11/1977 | Kline | 604/164 |
| 4,239,042 | 12/1980 | Asai | 604/164 |
| 4,424,833 | 1/1984 | Spector et al. | 604/167 X |
| 4,430,081 | 2/1984 | Timmermans | 604/167 X |
| 4,451,256 | 5/1984 | Weikl et al. | 604/164 |
| 4,468,224 | 8/1984 | Enzmann et al. | 604/164 X |

Primary Examiner—Dalton L. Truluck
Attorney, Agent, or Firm—Frishauf, Holtz, Goodman & Woodward

[57] ABSTRACT

An instrument for introducing a catheter into a blood vessel includes an inner needle portion having an inner needle, and a dilator portion having a dilator, the latter including first and second insertion portions. The first insertion portion, which has a comparatively small diameter and a length no less than the distance from a patient's skin to the blood vessel wall, is formed at the tip of the dilator from which a cutting edge at the tip of the inner needle is capable of protruding. The second insertion portion, which has a comparatively large diameter and a length no less than the above length, is smoothly connected to the first insertion portion by a tapered intermediate segment. Also provided is a sheath portion through which a catheter is capable of being passed under liquid-tight conditions.

9 Claims, 18 Drawing Figures

CATHETER INTRODUCING INSTRUMENT

BACKGROUND OF THE INVENTION

1. Field of the Invention

This invention relates to a catheter introducing instrument well-suited for introducing a catheter into a blood vessel.

2. Description of the Prior Art

In order to introduce a catheter into a blood vessel through the skin, the practice in the prior art is to use an introducing needle, a guide wire and a dilator. More specifically, the introducing needle, which comprises an inner needle portion and a cover tube, is used to pierce the desired blood vessel, after which only the inner needle portion is withdrawn. The guide wire is then inserted into the blood vessel by being passed through the cover tube, which has been left in place. This is followed by withdrawing the cover tube, leaving the guide wire in place. Next, the dilator is so inserted as to fit over the guide wire and functions to dilate the opening made in the subcutaneous tissue and in the wall of the blood vessel, thus making it possible to reduce resistance which the catheter meets in being inserted through the subcutaneous tissue and blood vessel wall. This is followed by withdrawing the dilator from the guide wire and fitting the catheter over the guide wire so that the catheter may then be introduced into the blood vessel.

The conventional method described above is disadvantageous in that the preparation and handling of the instruments is of some complexity, it being necessary to furnish the introducing needle, which makes it possible to insert the guide wire into the blood vessel so that the catheter can be introduced into the blood vessel through the skin, as well as the dilator for spreading the subcutaneous tissue and the opening in the blood vessel wall to facilitate the introduction of the catheter. Furthermore, since it is necessary to insert the guide wire into the blood vessel from the cover tube of the introducing needle, withdraw the cover tube and then insert the dilator into the blood vessel by fitting the dilator over the guide wire, it is required that the patient be punctured twice. This not only involves a complicated operating procedure but also subjects the patient to a considerable burden.

SUMMARY OF THE INVENTION

An object of the present invention is to simplify the handling of the instruments and to facilitate the operation involved in inserting a catheter into a blood vessel.

Another object of the present invention is to prevent backflow of blood when a catheter is introduced into a blood vessel.

According to the present invention, the foregoing object is attained by providing an instrument for introducing a catheter into a blood vessel. In one aspect of the invention, the instrument comprises an inner needle portion including an inner needle having a tip formed to include a cutting edge, and a dilator portion having a hollow dilator with a tip for enabling the inner needle to be passed therethrough until the cutting edge of the inner needle projects from the tip of the dilator. The dilator is formed to include a primary insertion portion having a prescribed outer diameter, a secondary insertion portion having an outer diameter larger than that of the primary insertion portion, and an intermediate tapered segment smoothly interconnecting the primary and secondary insertion portions. The primary insertion portion extends from the tip of the dilator to one end of the tapered segment over a length no less than a distance from a skin surface to a wall of the blood vessel, and the secondary insertion portion extends from another end of the tapered segment over a length no less than the distance from the skin surface to the wall of the blood vessel. Accordingly, the dilator performs two useful functions. First, it serves to insert the guide wire into the blood vessel so that the guide wire may subsequently introduce a catheter into the blood vessel by being passed through the skin. Second, the secondary insertion portion of the dilator serves to widen the opening formed in the subcutaneous tissue and in the blood vessel wall to facilitate the introduction of the guide wire. This arrangement facilitates and simplifies the catheter insertion procedure by making it possible to delete the prior-art steps of withdrawing a cover tube after the wire guide has been inserted into the blood vessel from the interior of the tube, and repuncturing the blood vessel by passing the dilator over the guide wire to insert the dilator into the blood vessel.

In a preferred embodiment of the present invention, the primary and secondary insertion portions of the dilator each have a length of no less than 15 mm, the outer diameter of the primary insertion portion is 1 to 3 mm, and that of the secondary insertion portion is 1.3 to 3 times that of the primary insertion portion. The wall thickness of the primary insertion portion of the dilator is 0.05 to 0.3 mm, and that of the secondary insertion portion is no less than 0.3 mm. These lengthwise dimensions assure that the primary and secondary insertion portions will each be able to pass through the subcutaneous tissue so that their leading ends may penetrate the interior of the blood vessel in a reliable manner. The stated range of outer diameter dimensions limits a change in insertion resistance at a stage where there is a transition from insertion of the primary insertion portion into the subcutaneous tissue and blood vessel wall to insertion of the secondary insertion portion into the subcutaneous tissue and blood vessel wall, and makes it possible for the secondary insertion portion to reliably widen the catheter introduction opening in the subcutaneous tissue and blood vessel wall to a degree necessary for insertion of the catheter.

In another aspect of the present invention, the instrument for inserting a catheter into a blood vessel comprises an inner needle portion including an inner needle having a tip formed to include a cutting edge, a dilator portion having a hollow dilator with a tip for enabling the inner needle to be passed therethrough until the cutting edge of the inner needle projects from the tip of the dilator, and the dilator comprises a primary insertion portion having a prescribed outer diameter, a secondary insertion portion having an outer diameter larger than that of the primary insertion portion, and an intermediate tapered segment smoothly interconnecting the primary and secondary insertion portions. A sheath portion includes a sheath for enabling the dilator to be passed therethrough, the sheath being so adapted that when the dilator is passed therethrough, a tip of the sheath portion is in proximity to an end of the secondary insertion portion of the dilator, and a valve body enables a catheter to be passed therethough under liquid-tight conditions. The primary insertion portion extends from the tip of the dilator to one end of the tapered segment over a length no less than a distance from a skin surface to a wall of the blood vessel, and the secondary insertion portion extends from another end of the tapered segment over a length no less than the distance from the skin surface to the wall of the blood vessel. Accordingly, the dilator serves to insert the guide wire into the blood vessel so that the guide wire may subsequently introduce a catheter into the blood vessel by being passed through the skin. The secondary insertion portion of the dilator serves to widen the opening formed in the subcutaneous tissue and in the blood vessel wall to facilitate the introduction of the sheath. Since the catheter introducing instrument of the present invention includes the inner needle, introduction into the blood vessel is possible though a simple operation without using a Seldinger needle.

In a preferred embodiment of this arrangement, the primary and secondary insertion portions of the dilator each have a length of no less than 15 mm, the outer diameter of the primary insertion portion is 1 to 3 mm, and that of the secondary insertion portion is 1.3 to 3 times that of the primary insertion portion. The wall thickness of the primary insertion portion of the dilator is 0.05 to 0.3 mm, and that of the secondary insertion portion is no less than 0.3 mm. These dimensions bring forth the advantages described above.

The valve body of the sheath portion consists of a flexible, elastic material and has a first end face provided with an elongated first incision and a second end face provided with an elongated second incision. The first and second incisions are formed so as to intersect each other inside the valve body without passing entirely therethrough. The catheter is passed through the valve body where the first and second incisions intersect. This construction of the valve body prevents backflow of the patient's blood when the catheter is inserted into the blood vessel.

The sheath portion further comprises a housing for fixedly retaining a base end portion of the sheath, the housing internally accommodating the valve body at the base end of the sheath.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Figure 1:
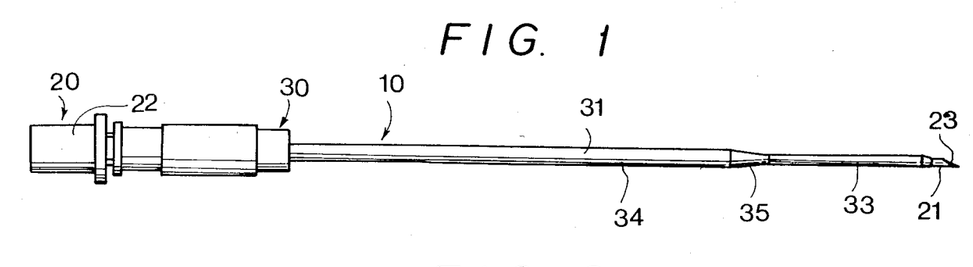
FIG. 1 is a side view illustrating a first embodiment of a catheter introducing instrument according to the present invention.
Figure 2:
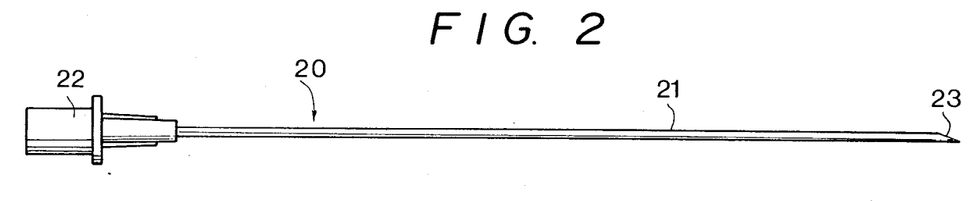
FIG. 2 is a side view illustrating an inner needle portion shown extracted from the catheter introducing instrument of the first embodiment.
Figure 3:
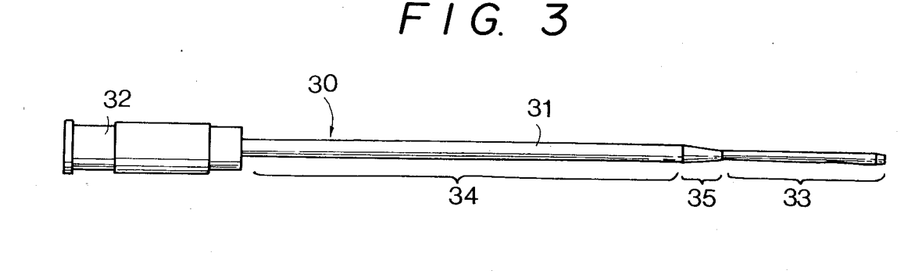
FIG. 3 is a side view illustrating a dilator portion shown extracted from the catheter introducing instrument according to the first embodiment.

With reference first to FIGS. 1 through 3, a first embodiment of a catheter introducing instrument 10 according to the present invention comprises an inner needle portion 20 and a dilator portion 30. The inner needle portion 20, which is shown extracted from the instrument in the side view of FIG. 2, comprises an inner needle 21, which may be either hollow or solid, and a hub 22 fixedly supporting the base end portion of the inner needle 21. The tip of the inner needle 21 has a cutting edge 23. The inner needle 21 is made of stainless steel and the hub 22 of a polycarbonate resin, by way of example.

The dilator portion 30, which is shown extracted from the instrument in the side view of FIG. 3, comprises a hollow dilator 31 through which the inner needle 21 is capable of being passed until the cutting edge 23 of the needle projects from the tip of the dilator, and a hub 32 fixedly supporting the base end portion of the dilator 31. The dilator 31 is formed to include a primary insertion portion 33 and a secondary insertion portion 34, as shown in FIG. 3. The primary insertion portion 33, which forms the tip of the dilator 31 from which the cutting edge 23 of the inner needle 21 is capable of being projected, is of a comparatively small outer diameter and has a length greater than the distance from the skin surface to the blood vessel wall that is needed to puncture the blood vessel. This distance shall be referred to as the "puncture distance" hereafter. The secondary insertion portion 34, which is smoothly connected to the primary insertion portion 33 by a tapered segment 35, is of a comparatively large diameter and has a length greater than the aforementioned puncture distance. The primary insertion portion 33 is capable of being inserted through subcutaneous tissue and through the wall of a blood vessel with the cutting edge 23 of the inner needle projecting from the tip of the dilator 31. The secondary insertion portion 34 is capable of being inserted through the subcutaneous tissue and through the blood vessel wall along a guide wire which is passed through the dilator 31 so as to be positioned ahead of the tip of the dilator 31. The secondary insertion portion 34 serves to spread or dilate the opening formed in the subcutaneous tissue and in the blood vessel wall for the introduction of the catheter. In order to reduce the puncture resistance of the dilator 31, the tip thereof is rounded or tapered.

As mentioned above, the primary and secondary insertion portions 33, 34 of the dilator 31 are at least long enough to enable each to penetrate the subcutaneous tissue and blood vessel wall. Preferably, each has a length of no less than 15 mm, which will allow the respective leading ends thereof to reach the interior of the blood vessel in reliable fashion. The secondary insertion portion 34 of the dilator 31 preferably has an outer diameter of 1 to 3 mm, which is between 1.3 to 3 times the outer diameter of the primary insertion portion 33. This is to limit a change in insertion resistance at a stage where there is a transition from insertion of the primary insertion portion 33 into the subcutaneous tissue and blood vessel wall to insertion of the secondary insertion portion 34 into the subcutaneous tissue and blood vessel wall. Such a design also makes it possible for the secondary insertion portion 34 to reliably widen the introduction opening in the subcutaneous tissue and blood vessel wall to a degree necessary for insertion of the catheter. Preferably, the wall thickness of the primary insertion portion 33 is selected to be between 0.05 and 0.3 mm, and that of the secondary insertion portion 34 no less than 0.3 mm. Since the primary insertion portion 33 is eventually fully inserted into the blood vessel, it is preferred that this portion be flexible so as not to injure the blood vessel wall.

The dilator 31 consists of, e.g., a fluoroplastic, a polyamide resin, a polyester resin, polyethylene or polypropylene, and the hub 32 consists of, e.g., polyamide resin. The surface of the dilator 31 preferably is coated with a thrombus preventing material such as polyhydroxyethyl methacrylate (polyhema), a block copolymer of hema-st-hema, or the like. Preferably, an X-ray image forming agent such as barium sulfate or bismuth carbonate is blended into the material constituting the dilator 31, or image forming filaments formed by blending the dilator material and the X-ray image forming agent are imbedded in the dilator.

It is possible to form the primary and secondary insertion portions 33, 34 in an extrusion molding operation by drawing the primary insertion portion 33 at a certain rate and drawing the secondary insertion portion 34 at a different rate. Alternatively, the tip of a mold-hardened tube may be pulled to form the primary insertion portion 33 on the tip side and the secondary insertion portion 34 on the side opposite. Still another possibility is to clad a small-diameter tube, with the exception of the tip portion thereof, with a large-diameter tube, the small-diameter tube forming the primary insertion portion 33 and the large diameter tube the secondary insertion portion 34.

Let us now refer to the sectional views of FIGS. 4(A) through 4(D) to describe a method of using the above-described catheter introducing instrument 10 of the first embodiment.

Figure 4:
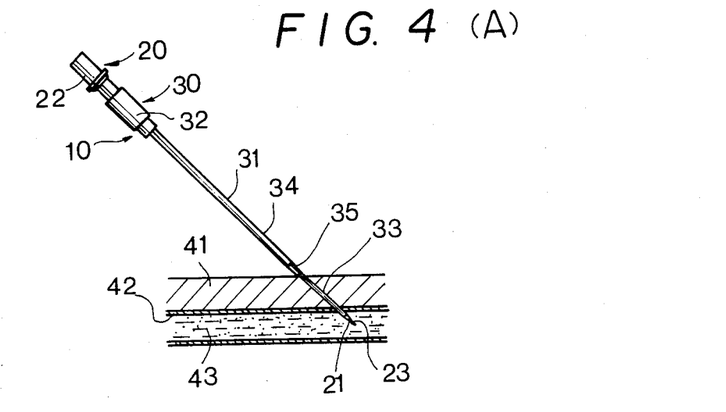
FIGS. 4(A) through 4(D) are sectional views illustrating a method of using the catheter introducing instrument according to the first embodiment.
Figure 5:
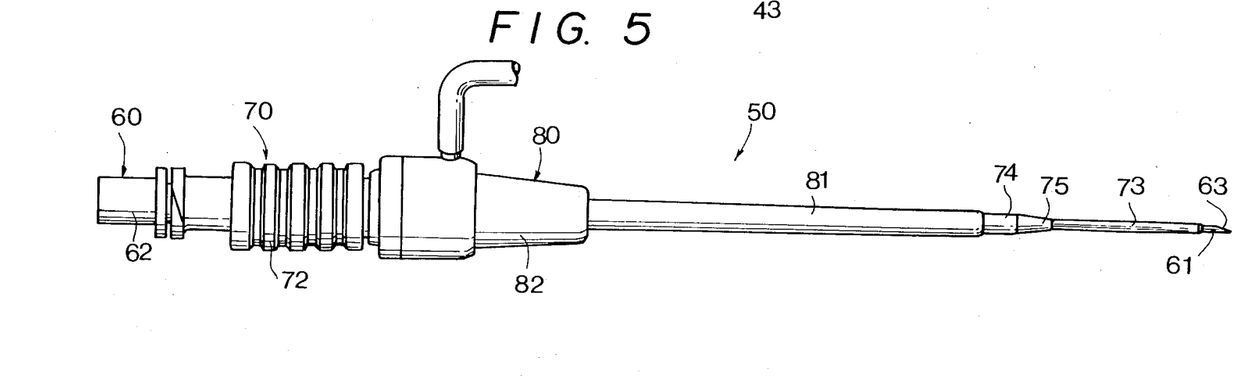
FIG. 5 is a side view illustrating a second embodiment of a catheter introducing instrument according to the present invention.
Figure 6:
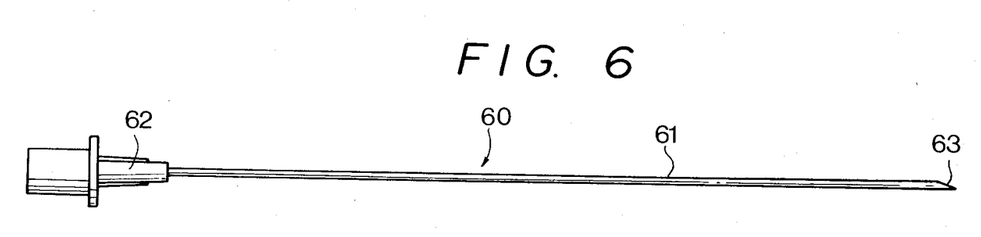
FIG. 6 is a side view illustrating an inner needle portion shown extracted from the catheter introducing instrument according to the second embodiment.

As shown in (A) of FIG. 4, the instrument 10 pierces subcutaneous tissue 41 and a blood vessel wall 42. More specifically, the cutting edge 23 of the inner needle 21 projecting from the tip of the dilator 31 punctures the tissue 41 and the blood vessel wall 42 to form an opening that immediately receives the tip of the dilator 31. The fact that the cutting edge 23 of the inner needle 21 and the tip of the dilator 31 have reached the blood vessel is confirmed by flashback, namely a phenomenon wherein blood flows back along the needle due to the pressure of the blood internally of the blood vessel. At this stage only the primary insertion portion 33 of the dilator 31 penetrates the body. Next, as shown in (B) of FIG. 4, the inner needle 21 is withdrawn through the interior of the dilator 31 by pulling back on the needle hub 22, leaving the dilator portion 30 of the instrument 10 in place. The primary insertion portion 33 therefore remains in the inserted state. The next step, shown in (C) of FIG. 4, is to insert a guide wire 44 into the blood vessel 43 from the rear of the dilator portion 30, with the tip of the guide wire 44 being forced about 10 cm into the blood vessel 43 from the tip of the dilator 31. This is followed by inserting, along the guide wire 44, the secondary insertion portion 34 of the dilator 31 into the blood vessel 43 while rotating the dilator portion 30. The secondary insertion portion 34 thus widens the opening formed in the subcutaneous tissue 41 and blood vessel wall 42 for the subsequent insertion of a catheter 45. Next, as shown in (D) of FIG. 4, the dilator portion 30 of the instrument 10 is withdrawn from the guide wire 44, leaving the guide wire in place. The catheter 45 is then slipped over the guide wire 44 and is inserted into the blood vessel 43 under the guidance of the wire. The insertion of the catheter 45 into the blood vessel 43 at this time is facilitated since the catheter insertion opening formed in the subcutaneous tissue 41 and blood vessel wall 42 has been widened by the secondary insertion portion 44 of the dilator 31, already withdrawn.

Excellent operability was verified using a catheter introducing instrument 10 in which the inner needle 21 was made of stainless steel, the hub 22 of a polycarbonate resin, the dilator 31 of a fluoroplastic and the hub 32 of a polyamide resin, and in which the length and outer diameter of the primary insertion portion 33 were 20 mm and 1.4 mm, respectively, the length and outer diameter of the secondary insertion portion 34 were 55 mm and 2 mm, respectively, and the length of the tapered portion 35 was 5 mm.

Reference will now be had to FIGS. 5 through 8 to describe a second embodiment of a catheter introducing instrument according to the present invention. The instrument, shown at numeral 50, comprises an inner needle portion 60, a dilator portion 70 and a sheath portion 80. The inner needle portion 60, which is shown extracted from the instrument 50 in the side view of FIG. 6, comprises an inner needle 61 and a hub 62 fixedly supporting the base end portion of the inner needle 61. The tip of the inner needle 61 has a cutting edge 63.

Figure 7:
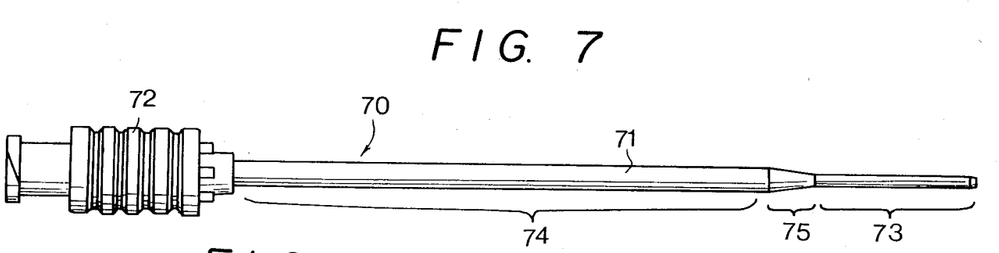
FIG. 7 is a side view illustrating a dilator portion shown extracted from the catheter introducing instrument according to the second embodiment.

The dilator portion 70, which is shown extracted from the instrument 50 in the side view of FIG. 7, comprises a dilator 71 through which the inner needle 61 is capable of being passed until the cutting edge 63 of the needle projects from the distal end of the dilator, and a hub 72 fixedly supporting the base end portion of the dilator 71. The dilator 71 is formed to include a primary insertion portion 73 and a secondary insertion portion 74, as shown in FIG. 7. The primary insertion portion 73, which forms the tip of the dilator 71 from which the cutting edge 63 of the inner needle 61 is capable of being projected, is of a comparatively small outer diameter. The secondary insertion portion 74, which is smoothly connected to the primary insertion portion 73 by a tapered segment 75, is of a comparatively large diameter. The primary and secondary insertion portions 73, 74 of the dilator 71 are long enough to enable each to penetrate the subcutaneous tissue and blood vessel wall. Specifically, each has a length of no less than 15 mm, which will allow the respective ends thereof to reach the interior of the blood vessel in reliable fashion. The secondary insertion portion 74 of the dilator 71 preferably has an outer diameter of 1 to 3 mm, which is between 1.3 to 3 times the outer diameter of the primary insertion portion 73. This is to suppress a change in insertion resistance at a stage where there is a transition from insertion of the primary insertion portion 73 into the subcutaneous tissue and blood vessel wall to insertion of the secondary insertion portion 74 into the subcutaneous tissue and blood vessel wall. Such a design als makes it possible for the secondary insertion portion 74 to reliably widen the introduction opening in the subcutaneous tissue and blood vessel wall to a degree necessary for insertion of the catheter. Preferably, the thickness of the primary insertion portion 73 is selected to be between 0.05 and 0.3 mm, and that of the secondary insertion portion 74 no less than 0.3 mm.

It is possible to form the primary and secondary insertion portions 73, 74 in an extrusion molding operation by drawing the primary insertion portion 73 at a certain rate and drawing the secondary insertion portion 74 at a different rate. Alternatively, the tip of a mold-hardened tube may be pulled to form the primary insertion portion 73 on the tip side and the secondary insertion portion 74 on the side opposite. Still another possibility is to clad a small-diameter tube, with the exception of the tip portion thereof, with a large-diameter tube, the small-diameter tube forming the primary insertion portion 73 and the large diameter tube the secondary insertion portion 74.

Figure 8:
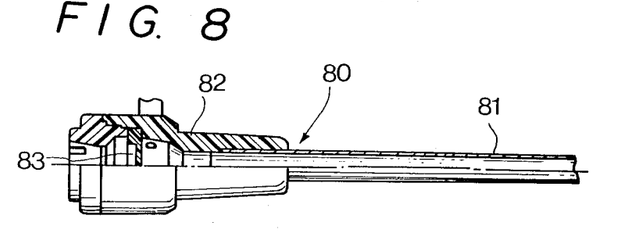
FIG. 8 is a partially sectional view illustrating a sheath shown extracted from the catheter introducing instrument according to the second embodiment.

The sheath portion 80, which is shown extracted from the instrument 50 in the partially sectional view of FIG. 8, comprises a sheath 81 through which the secondary insertion portion 74 of the dilator 71 is capable of being passed, a housing 82 for fixedly retaining the base end portion of the sheath 81, and a backflow preventing valve 83 incorporated in the housing 82 for being brought into intimate contact with the outer peripheral surface of the dilator 71. The sheath 81 is capable of receiving a catheter passed therethrough, with the backflow preventing valve 83 coming into intimate contact with the outer peripheral surface of the catheter to prevent an extracorporeal backflow of the patient's blood when the catheter is introduced.

Figure 9:
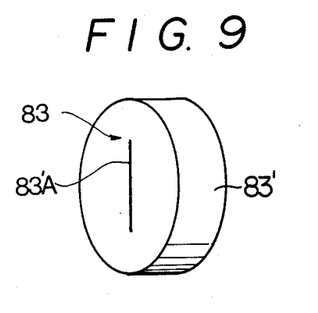
FIG. 9 is a perspective view illustrating a backflow preventing valve according to the second embodiment.
Figure 10:
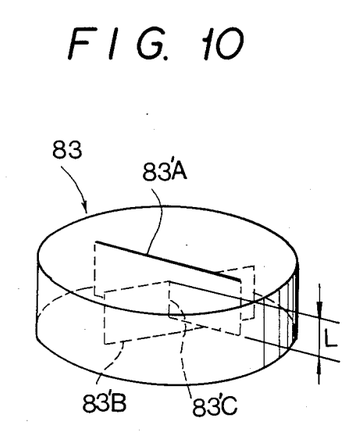
FIG. 10 is a perspective view illustrating the internal structure of the valve shown in FIG. 9.

The backflow preventing valve 83 is made of a synthetic rubber such as silicone rubber, urethane rubber or fluororubber, or natural rubber or of any other material exhibiting flexibility and elasticity. As shown in the perspective views of FIGS. 9 and 10, the backflow preventing valve 83 comprises a valve body 83' having a first end face provided with an elongated first incision 83'A and a second end face provided with an elongated second incision 83'B. The first and second incisions 83'A, 83'B do not pass entirely through the thickness of the valve body 83' but intersect internally of the valve body 83' to form an intersection 83'C having a length L. This construction allows a catheter to be passed through the first and second incisions 83'A, 83'B and through their intersection 83'C as the valve body 83' undergoes elastic deformation caused by the insertion of the catheter. Accordingly, even if the catheter has a comparatively large outer diameter, the incisions 83'A 83'B continuously pressure the catheter to prevent the formation of gaps at the periphery thereof as the catheter is passed longitudinally through the valve 83. Since the valve 83 is made of an elastic, flexible material as mentioned above, the incised portions of the valve body 83' come into substantially liquid-tight surface contact with the periphery of the catheter.

A method of using the above-described catheter introducing instrument 50 of the second embodiment of the present invention will now be described with reference to the sectional views of FIGS. 11(A) through 11(E).

Figure 11:
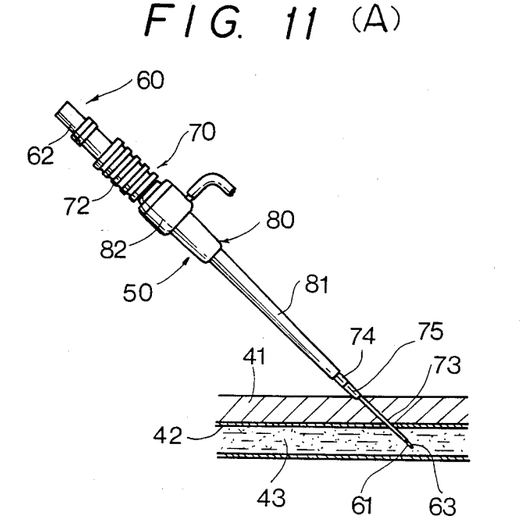
FIGS. 11(A) through 11(E) are sectional views illustrating a method of using the catheter introducing instrument according to the second embodiment.

As shown in (A) of FIG. 11, the instrument 50 pierces the subcutaneous tissue 41 and the blood vessel wall 42 in the manner described above with reference to the first embodiment of the invention. The fact that the cutting edge 63 of the inner needle 61 and the tip of the dilator 71 have reached the blood vessel is confirmed by flashback. At this stage only the primary insertion portion 73 of the dilator 71 penetrates the patient's body. Next, as shown in (B) of FIG. 11, the inner needle 60 is withdrawn through the interior of the dilator 71 by pulling back on the needle hub 62, leaving the dilator portion 70 of the instrument 50 in place. The primary insertion portion 73 therefore remains in the inserted state. The next step, shown in (C) of FIG. 1, is to insert the guide wire 44 into the blood vessel 43 from the rear of the dilator portion 70, with the tip of the guide wire 44 being forced about 10 cm into the blood vessel 43 from the tip of the dilator 71. This is followed by inserting, along the guide wire 44, both the secondary insertion portion 74 of the dilator 71 and the sheath 81 into the blood vessel 43 while rotating both the dilator portion 70 and the sheath portion 80, as shown in (D) of FIG. 11. Next, as shown in (E) of FIG. 11, the dilator portion 70 of the instrument 50 and the guide wire 44 are withdrawn from the interior of the sheath 81, leaving the sheath 81 in place penetrating the blood vessel 43. The catheter 45 is passed through the interior of the sheath 81 and is inserted into the blood vessel 43. This completes the introduction of the catheter 45.

EFFECT OF THE INVENTION

As aforesaid, according to the present invention, the instrument comprises an inner needle portion including an inner needle having a tip formed to include a cutting edge, and a dilator portion having a hollow dilator with a tip for enabling the inner needle to be passed therethrough until the cutting edge of the inner needle projects from the tip of the dilator. The dilator is formed to include a primary insertion portion having a prescribed outer diameter, a secondary insertion portion having an outer diameter larger than that of the primary insertion portion, and an intermediate tapered segment smoothly interconnecting the primary and secondary insertion portions. The primary insertion portion extends from the tip of the dilator to one end of the tapered segment over a length no less than a distance from a skin surface to a wall of the blood vessel, and the secondary insertion portion extends from another end of the tapered segment over a length no less than the distance from the skin surface to the wall of the blood vessel. Accordingly, the dilator performs two useful functions. First, it serves to insert the guide wire into the blood vessel so that the guide wire may subsequently introduce a catheter into the blood vessel by being passed through the skin. Second, the secondary insertion portion of the dilator serves to widen the opening formed in the subcutaneous tissue and in the blood vessel wall to facilitate the introduction of the guide wire. This arrangement facilitates and simplifies the catheter insertion procedure by making it possible to delete the prior-art steps of withdrawing a cover tube after the wire guide has been inserted into the blood vessel from the interior of the tube, and repuncturing the blood vessel by passing the dilator over the guide wire to insert the dilator into the blood vessel.

In a preferred embodiment of the present invention, the primary and secondary insertion portions of the dilator each have a length of no less than 15 mm, the outer diameter of the primary insertion portion is 1 to 3 mm, and that of the secondary insertion portion is 1.3 to 3 times that of the primary insertion portion. The wall thickness of the primary insertion portion of the dilator is 0.05 to 0.3 mm, and that of the secondary insertion portion is no less than 0.3 mm. These lengthwise dimensions assure that the primary and secondary insertion portions will each be able to pass through the subcutaneous tissue so that their leading ends may penetrate the interior of the blood vessel in a reliable manner. The stated range of outer diameter dimensions limits a change in insertion resistance at a stage where there is a transition from insertion of the primary insertion portion into the subcutaneous tissue and blood vessel wall to insertion of the secondary insertion portion into the subcutaneous tissue and blood vessel wall, and makes it possible for the secondary insertion portion to reliably widen the catheter introduction opening in the subcutaneous tissue and blood vessel wall to a degree necessary for insertion of the catheter.

In another aspect of the present invention, the instrument for inserting a catheter into a blood vessel comprises an inner needle portion including an inner needle having a tip formed to include a cutting edge, a dilator portion having a hollow dilator with a tip for enabling the inner needle to be passed therethrough until the cutting edge of the inner needle projects from the tip of the dilator, and the dilator comprises a primary insertion portion having a prescribed outer diameter, a secondary insertion portion having an outer diameter larger than that of the primary insertion portion, and an intermediate tapered segment smoothly interconnecting the primary and secondary insertion portions. A sheath portion includes a sheath for enabling the dilator to be passed therethrough, the sheath being so adapted that when the dilator is passed therethrough, a tip of the sheath portion is in proximity to an end of the secondary insertion portion of the dilator, and a valve body enables a catheter to be passed therethough under liquid-tight conditions. The primary insertion portion extends from the tip of the dilator to one end of the tapered segment over a length no less than a distance from a skin surface to a wall of the blood vessel, and the secondary insertion portion extends from another end of the tapered segment over a length no less than the distance from the skin surface to the wall of the blood vessel. Accordingly, the dilator serves to insert the guide wire into the blood vessel so that the guide wire may subsequently introduce a catheter into the blood vessel by being passed through the skin. The secondary insertion portion of the dilator serves to widen the opening formed in the subcutaneous tissue and in the blood vessel wall to facilitate the introduction of the sheath. Since the catheter introducing instrument of the present invention includes the inner needle, introduction into the blood vessel is possible though a simple operation without using a Seldinger needle.

In a preferred embodiment of this arrangement, the primary and secondary insertion portions of the dilator each have a length of no less than 15 mm, the outer diameter of the primary insertion portion is 1 to 3 mm, and that of the secondary insertion portion is 1.3 to 3 times that of the primary insertion portion. The wall thickness of the primary insertion portion of the dilator is 0.05 to 0.3 mm, and that of the secondary insertion portion is no less than 0.3 mm. These dimensions bring forth the advantages described above.

The valve body of the sheath portion consists of a flexible, elastic material and has a first end face provided with an elongated first incision and a second end face provided with an elongated second incision. The first and second incisions are formed so as to intersect each other inside the valve body without passing entirely therethrough. The catheter is passed through the valve body where the first and second incisions intersect. This construction of the valve body prevents backflow of the patient's blood when the catheter is inserted into the blood vessel.

The sheath portion further comprises a housing for fixedly retaining a base end portion of the sheath, the housing internally accommodating the valve body at the base end of the sheath.

As many apparently widely different embodiments of the present invention can be made without departing from the spirit and scope thereof, it is to be understood that the invention is not limited to the specific embodiments thereof expect as defined in the appended claims.

What we claimed is:

1. An instrument for introducing a catheter into a blood vessel, comprising:
    an inner needle portion including an inner needle having a tip formed to include a cutting edge; and
    a dilator portion including a hollow dilator having a rounded or tapered tip, for enabling said inner neddle to be passed therethrough until the cutting edge of said inner needle projects from the rounded tip of said dilator;
    said dilator comprising a primary insertion portion having a length of at least 15 mm and a wall thickness of 0.05 mm to 0.3 mm;
    a secondary insertion portion having a length of at least 15 mm, an outer diameter of between 1.3 to 3.0 times that of said primary insertion portion, and a wall thickness of at least 0.3 mm; and
    an intermediate tapered segment smoothly interconnecting said primary and said secondary insertion portions;
    wherein operations of puncture and widening of subcutaneous tissue and blood vessel walls prior to insertion of a catheter can be performed with simultaneous advancement of said inner needle and said dilator through the body of a patient.

2. The instrument according to claim 1, wherein said primary insertion portion is made of a flexible and elastic material.

3. The instrument according to claim 1, wherein the surface of the dilator is coated with a thrombus preventing material.

4. An instrument for introducing a catheter into a blood vessel, comprising:
    an inner needle portion including an inner needle having a tip formed to include a cutting edge;
    a dilator portion including a hollow dilator having a rounded or tapered tip, for enabling said inner needle to be passed therethrough until the cutting edge of said inner needle projects from the rounded tip of said dilator;
    said dilator comprising a primary insertion portion having a length of at least 15 mm and a wall thickness of 0.05 mm to 0.3 mm;
    a secondary insertion portion having a length of at least 15 mm, an outer diameter of between 1.3 to 3.0 times that of said primary insertion portion, and a wall thickness of at least 0.3 mm; and
    an intermediate tapered segment smoothly interconnecting said primary and said secondary insertion portions; and
    a sheath portion comprising a sheath for enabling said dilator to be passed therethrough, the sheath being so adapted that when the dilator is passed therethrough, a tip of the sheath portion is in proximity to an end of said secondary insertion portion of the dilator, and a valve body for enabling a catheter to be passed therethrough under liquid-tight conditions;

wherein operations of puncture and widening of subcutaneous tissue and blood vessel walls prior to insertion of catheter can be performed with simultaneous advancement first of said inner needle and said dilator and then of said dilator and said sheath through the body of a patient.

5. The instrument according to claim 4, wherein said valve body consists of a flexible, elastic material and has a first end face provided with an elongated first incision and a second end face provided with an elongated second incision, said first and second incisions being formed so as to intersect each other internally of said valve body without passing entirely therethrough.

6. The instrument according to claim 4, wherein said sheath portion further comprises a housing for fixedly retaining a base end portion of said sheath.

7. The instrument according to claim 6, wherein said housing internally accommodates said valve body in the vicinity of the base end portion of said sheath.

8. The instrument according to claim 4, wherein said primary insertion portion is made of a flexible and elastic material.

9. The instrument according to any one of claim 4, wherein the surface of the dilator is coated with a thrombus preventing material.

* * * * *